United States Patent [19]

Selby

[11] Patent Number: 5,587,522
[45] Date of Patent: Dec. 24, 1996

[54] MULTIPLE-PART AND/OR SUPPORTED GAS-CONTAINING VESSEL TO ESTABLISH DESIRED HEAT FLUX

[76] Inventor: Theodore W. Selby, 4402 Arbor Dr., Midland, Mich. 48640

[21] Appl. No.: 577,969

[22] Filed: Dec. 26, 1995

[51] Int. Cl.[6] .............. F25D 23/06; F25D 1/00; B65D 81/38
[52] U.S. Cl. .............. 73/54.28; 73/54.43; 73/25.01; 73/430; 62/383; 62/451; 374/33
[58] Field of Search .............. 73/54.28, 54.43, 73/25.01, 54.35; 62/383, 430, 451; 374/33

[56] References Cited

U.S. PATENT DOCUMENTS

| | | | |
|---|---|---|---|
| 2,801,526 | 8/1957 | Solley, Jr. | 62/6 |
| 3,024,941 | 3/1962 | Vandenberg | 220/63 |
| 3,225,820 | 12/1965 | Riordan | 165/26 |
| 3,410,103 | 11/1968 | Cornelius | 62/136 |
| 3,654,773 | 4/1972 | White | 62/371 |
| 3,782,128 | 1/1974 | Hampton et al. | 62/51 |
| 4,137,964 | 2/1979 | Buckley | 165/1 |
| 4,241,601 | 12/1980 | Pennington, Sr. et al. | 73/17 R |
| 4,306,387 | 12/1981 | Hopkins et al. | 52/1 |
| 4,388,814 | 6/1983 | Schilling | 62/62 |
| 4,643,021 | 2/1987 | Mattout | 73/59 |
| 5,040,410 | 8/1991 | Chu et al. | 73/54 |
| 5,526,681 | 6/1996 | Selby | 73/54.43 |

OTHER PUBLICATIONS

ASTM D 2983–87 (Reapproved 1993).
Brookfield Viscometers/Rheometers Catalog, Brookfield Engineering Laboratories, Inc., Stoughton, Mass., 1993, pp. 10–11, 14–15 & 21–22.
Selby et al., *SAE Transactions*, vol. 68, 1968, pp. 457–467.
Tannas Co., Catalog, Tannas Co., Midland, Mich., 1994, p. 10.

*Primary Examiner*—Hezron E. Williams
*Assistant Examiner*—J. David Wiggins
*Attorney, Agent, or Firm*—Christopher John Rudy

[57] ABSTRACT

Vessel, useful in heat transmission regulation, includes a sealable, outer housing and a sample compartment generally enclosed therein such that a hollow portion between at least a part of the housing and compartment is present. The hollow compartment can contain a predetermined quantity of a gas. The sample compartment may be supported, and a multiple-part vessel can be provided. Such a vessel can be made to include standard-manufacture components, being easy to make and use, and/or be especially useful in viscosity testing.

22 Claims, 2 Drawing Sheets

MULTIPLE-PART AND/OR SUPPORTED GAS-CONTAINING VESSEL TO ESTABLISH DESIRED HEAT FLUX

FIELD

This invention concerns an apparatus having a sealable hollow housing about a sample compartment, which may be in multiple parts and/or which may be supported, and heat transmission and its regulation.

BACKGROUND

Theodore W. Selby in U.S. patent application Ser. No. 08/425,587 filed Apr. 20, 1995, which is incorporated herein by reference and which is now U.S. Pat. No. 5,526,681 (Jun. 18, 1996), has disclosed a gas-containing vessel to establish desired heat flux. Such a vessel, i.e., one useful for heat transmission regulation comprising a sealable, hollow housing about a sample compartment wherein a hollow portion of the housing contains a predetermined amount of a gas, and method to employ it in viscosity testing, e.g., in an improvement of the ASTM D 2983 protocol, are significant improvements in the art.

Nevertheless, room exists for further improvements.

SUMMARY

The present invention provides a vessel comprising a sealable, outer housing and a sample compartment generally enclosed therein such that a hollow portion between at least a part of the housing and compartment is present which can contain a predetermined quantity of a gas. The sample compartment may be supported.

The invention is useful in heat transmission regulation.

Significantly, by the invention, a multiple-part vessel, useful in heat transmission regulation, can be provided. Such a vessel can be made to include standard-manufacture components, being easy to make and use, and/or be especially useful in viscosity testing.

Numerous further advantages attend the invention.

DRAWINGS

The drawings form part of the specification hereof. With respect to the drawings, the following is briefly noted:

ILLUSTRATIVE DETAIL

The invention may be further understood with reference to certain embodiments and the drawings thereof. These are to be taken in an illustrative, and not necessarily limiting, sense.

Figure 1:
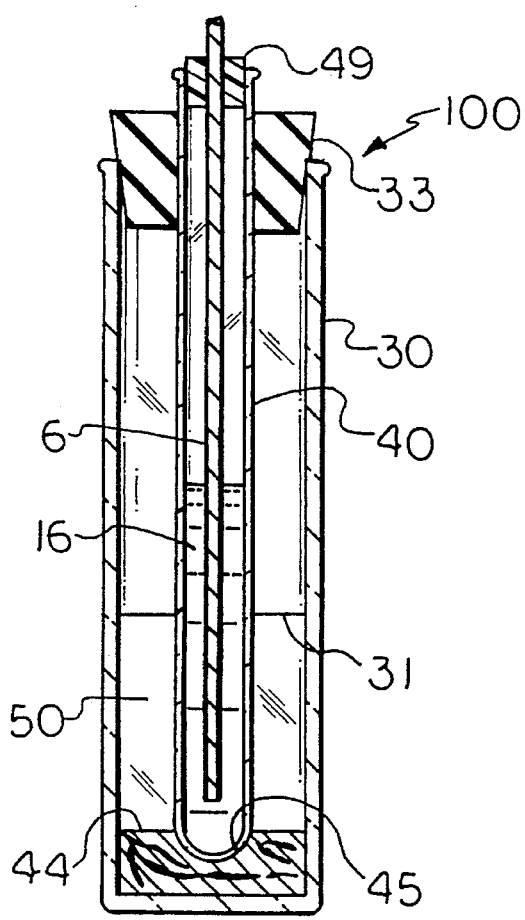
FIG. 1 is a side, cut-away view of a multiple-part and/or supported gas-containing vessel to establish desired heat flux of the present invention.
Figure 2:
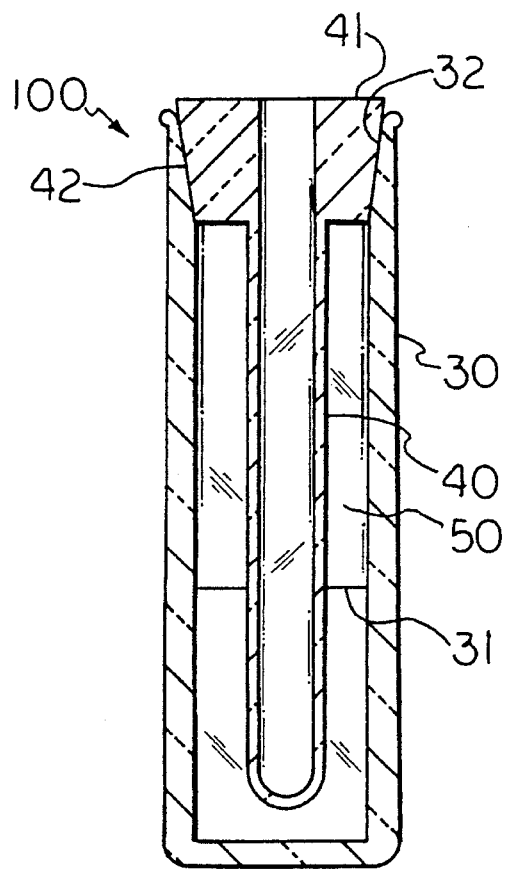
FIG. 2 is a side, cut-away view of another embodiment of a multiple-part and/or supported gas-containing vessel to establish desired heat flux of the invention.
Figure 3:
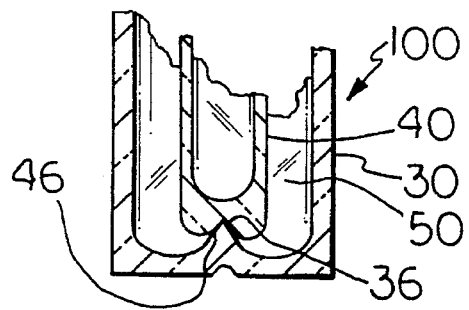
FIG. 3 is a side, cut-away view of a salient part of yet another embodiment of a multiple-part and/or supported gas-containing vessel to establish desired heat flux hereof.
Figure 4:
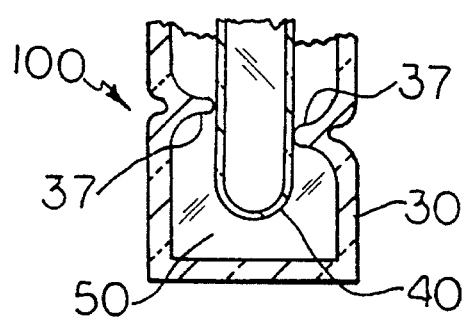
FIG. 4 is a side, cut-away view of a salient part of still another embodiment of a multiple-part and/or supported gas-containing vessel to establish desired heat flux hereof.
Figure 5:
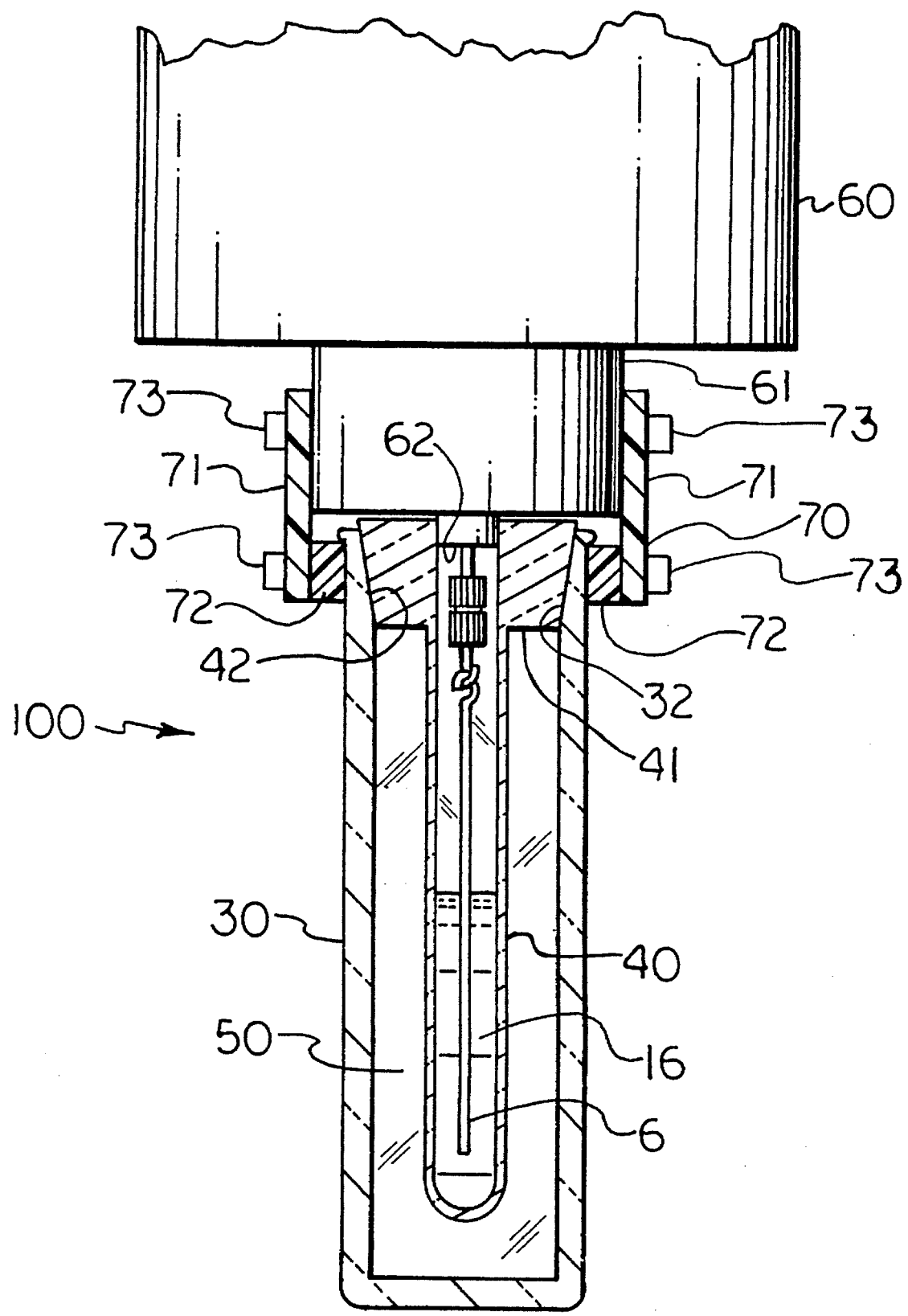
FIG. 5 is a side, partial cut-away view of a further embodiment of a multiple-part and/or supported gas-containing vessel to establish desired heat flux of the invention, attached to a sensitive rotating viscometer for viscosity testing.

In reference to FIGS. 1–5, vessel 100 includes outer housing 30 and a sample compartment 40. The outer housing 30 generally encloses the sample compartment 40, and the housing 30 and sample compartment 40 as an assembly are sealable. A hollow portion 50, which can contain a predetermined quantity of a gas, is present between the housing 30 and the sample compartment 40. As seen in FIGS. 1, 2 & 5, the vessel 100 can be of multiple parts, and the vessel 100 may be capable of assembly from or disassembly into such component parts including the outer housing 30 and the sample compartment 40. The vessel 100 may be capable of friction-fitting assembly from or disassembly into component parts of the outer housing 30, the sample compartment 40, and an optionally separate plug, or "stopper," to support the sample compartment 40 and to be received into the outer housing 30.

As depicted in FIGS. 1 & 2, the outer housing 30 can be a standard, cylindrical, glass pour point vial with pour point indicating line 31 etched on the outermost surface thereof. The vial may be plain (FIG. 1) or have a standard ground glass joint 32 (FIG. 2). As well, the outer housing may be another type of glass or plastic vessel such as a beaker, flask or test tube, and be not only of cylindrical or other radially symmetrical form but otherwise be of any suitable shape and material.

As depicted in FIG. 1, for a sealing support for the sample compartment 40, there may be provided one-hole stopper 33 such as of suitable composite such as of plastic or rubber, or such a stopper may be made of cork, wood, soft metal or other suitable material. The sample compartment 40, which may be in the form of a standard, cylindrical glass test tube or viscometer stator, is inserted into and through the hole of the stopper 33, which compartment and stopper assembly is inserted into the housing 30 to provide the vessel. As well, the sample compartment may be another type of glass or plastic vessel such as a beaker, flask or test tube, and be not only of cylindrical or other radially symmetrical form but otherwise be of any suitable shape and material.

As the gas within the hollow 50, the gas and its accompanying pressure can be selected to provide a known, predetermined value for a heat flux, and any gas often suffices. Ambient air is often employed.

The gas in the hollow may be of any suitable pressure to establish the desired heat flux. As can be appreciated accordingly, the hollow portion 50 with its predeterminable quantity of a gas therein can provide for a desired heat flux therethrough towards or away from a sample 16 in the sample compartment 40 depending upon factors including those associated with the predetermined quantity of a gas therein, and the temperatures of an external bath environment and the sample 16 in the sample compartment 40.

As depicted in FIGS. 2 & 5, one-piece sealing support and sample compartment 41 may be provided. It may be, for example, of blown or molded glass with a ground glass joint 42.

Support and centering for the sample compartment 40 may be provided by insert 44, which may be of a suitable thermally insulating substance, for an example, of balsa wood. Recess 45 receives and laterally stabilizes bottom of compartment 40. See, FIG. 1.

Support and centering for the sample compartment 40 may be provided by a bottom housing peak 36 in housing 30. The peak 36 registers with bottom sample compartment valley 46 to stabilize and support the sample compartment 40, especially to assist in providing lateral stability. Such a peak and valley arrangement may be provided in any suitable vessel, for an example, of glass. See, FIG. 3.

Support and centering for the sample compartment 40 may also be provided by a plurality of side housing peaks 37, say, three or even four, in housing 30. The peaks 37 approach or touch the outside of the sample compartment, and assist in providing lateral stability. Such side peaks may be provided in any suitable vessel, again, for example, of glass. See, FIG. 4.

The vessel 100 may be employed in viscosity testing, for example, in a test protocol akin to and an improvement over the ASTM D 2983 protocol. In such testing, rotor 6 is inserted in liquid sample 16, which may be oleaginous, in the sample compartment 40 which serves as the stator for a viscometric assembly. The sample 16, for example, an engine or gear oil or a transmission fluid, in the compartment 40 may be kept thermally stable by the vessel. As in FIG. 1, a two-hole (only the center hole, which is of a diameter slightly larger than that of the rotor 6, being depicted) sample compartment stopper 49, for example, of a suitable composite such as plastic or rubber, may be employed. A dry gas blanket, for example, of argon, nitrogen, air, and so forth, may be provided over the sample 16 by feeding the dry gas into the second hole (not depicted) which escapes through the space between the rotor 6 and the inside of the center hole of the stopper 49). As depicted in FIG. 5, with Brookfield rotational viscometer 60 having lower end 61, the inside of the sample compartment 40 is adapted to nest in standard cylindrical rotor-stabilizing protrusion 62 of the viscometer, with arrangement 70 including adapter 71 and stabilizing collar 72 being attachable to the viscometer by means of screws 73. The protrusion 62 may be made to be oversized, or a bushing or other spacing device may be added, to accommodate the inside of the sample compartment 40 being of a larger inside diameter than the protrusion. Provision may be made for a dry gas blanket over test liquid 16 such as by providing access to the inside of the sample compartment 40 about its upper end with hole(s) and/or tube(s) (not illustrated) and so forth and the like.

CONCLUSION

The present invention is thus provided. Numerous adaptations can be effected within its spirit, the literal claim scope of which is particularly pointed out as follows:

I claim:

1. A heat-insulating vessel comprising a sealable, outer housing and a sample compartment generally enclosed therein such that a hollow portion between walls of at least a part of the housing and sample compartment is present which can contain a predetermined quantity of a gas selected to have a known, predetermined value for a heat flux and which is supported within the housing by at least one peak in the vessel and/or by an added, thermally-insulative insert, said vessel being useful in heat transmission regulation therethrough between a sample, which can be provided within the sample compartment, and an external bath environment at a temperature T, said hollow portion with its predeterminable quantity of a gas therein able to provide for a desired heat flux therethrough towards or away from the sample depending upon factors including those associated with the predeterminable quantity of a gas therein, the temperature T of the external bath environment, and temperature of the sample within the sample compartment.

2. The vessel of claim 1, wherein the gas is present in said hollow portion, and the gas is air.

3. The vessel of claim 1, wherein the support includes at least on peak in the housing of the vessel on bottom and/or side wall(s) of the housing.

4. The vessel of claim 1, wherein the support is an added thermally insulative insert.

5. The vessel of claim 1, which is a multiple-part vessel.

6. The vessel of claim 5, wherein the housing and sample compartment include glass materials.

7. The vessel of claim 6, wherein ground glass joints are employed between the housing and compartment, the housing and compartment being generally cylindrical.

8. The vessel of claim 6, which is capable of friction-fitting assembly from or disassembly into components parts of the outer housing, the sample compartment, and a separate plug which can support the sample compartment and can be received into the outer housing.

9. The vessel of claim 7, wherein the gas is air.

10. A method of viscosity testing comprising, but necessarily in series, the following steps: providing a heat-insulating vessel having a sealable, outer housing and a sample compartment generally enclosed therein such that a hollow portion between walls of at least a part of the housing and sample compartment is present which can and does contain a predetermined quantity of a gas selected to have a known, predetermined value for a heat flux, said vessel being useful in heat transmission regulation therethrough between a sample within the sample compartment and an external bath environment at a temperature T; adding a liquid to be tested for viscosity as the sample to the sample compartment; establishing a desired temperature and degree of heat flux transfer or exchange for the liquid sample; and inserting a rotational viscometer rotor into the liquid sample, rotating the rotor while it is connected to a rotational viscometer, and determining the viscosity of the liquid sample therefrom, wherein a dry gas blanket is provided over the liquid sample.

11. The method of claim 10, wherein inside the sample compartment is generally cylindrical.

12. The method of claim 10, wherein the gas is air.

13. The method of claim 11, wherein the gas is air.

14. The method of claim 10, wherein the liquid is oleaginous.

15. In a method to test for viscosity of a liquid with a sensitive rotational viscometer having a rotor immersed in a sample of the liquid contained in a stator, wherein the sample is preconditioned with employment of a temperature control environment, the improvement comprising steps of (A) providing the stator in the form of a vessel useful for heat transmission regulation comprising a sealable, hollow housing about a sample compartment, a hollow portion of said housing containing a predetermined amount of a gas, wherein the housing has an external wall, and the sample compartment has a generally cylindrical internal wall, both walls defining the hollow portion;

(B) providing the sample and containing it in the sample compartment of the vessel;

(C) preconditioning the sample while it thus resides in the vessel, and then (D) testing the sample for viscosity with the sensitive rotational viscometer while the sample resides in the vessel, wherein a dry gas blanket is provided over the sample.

16. A heat-insulating vessel comprising a sealable, outer housing and a sample Compartment generally enclosed therein such that a hollow portion between walls of at least a part of the housing and sample compartment is present which can contain a predetermined quantity of a gas selected to have a known, predetermined value for a heat flux, said vessel being useful in heat transmission regulation therethrough between a sample, which can be provided within the sample compartment, and an external bath environment at a temperature T, said hollow portion with its predeterminable quantity of a gas therein able to provide for a desired heat flux therethrough towards or away from the sample depending upon factors including those associated with the predeterminable quantity of a gas therein, the temperature T of the external bath environment, and temperature of the sample within the sample compartment, wherein said vessel is a multiple-part vessel capable of assembly from or disassembly into component parts including the outer housing and the sample compartment, and support is provided the sample compartment when it is within the outer housing.

17. The vessel of claim 16, wherein as the sample compartment, a combination one-piece sealing support and sample compartment is provided, which is capable of assembly with the outer housing by its receipt thereinto and which provides support to the sample compartment thereby.

18. The vessel of claim 17, wherein the outer housing and combination one-piece sealing support and sample compartment include glass materials, and ground glass joints are employed between the outer housing and the combination one-piece sealing support and sample compartment.

19. The vessel of claim 18, wherein the outer housing and combination one-piece sealing support and sample compartment are generally cylindrical.

20. The vessel of claim 16, wherein the outer housing and sample compartment include glass materials, and ground glass joints are employed between the outer housing and sample compartment.

21. The vessel of claim 20, wherein the outer housing and sample compartment are generally cylindrical.

22. The vessel of claim 16, which is capable of friction-fitting assembly from or disassembly into components parts of the outer housing, the sample compartment, and a separate plug which can support the sample compartment and be received into the outer housing.

* * * * *